(12) United States Patent
Caren

(10) Patent No.: US 6,533,553 B2
(45) Date of Patent: *Mar. 18, 2003

(54) MICROFLUIDIC PUMPING

(75) Inventor: Michael P. Caren, Palo Alto, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/969,460

(22) Filed: Oct. 1, 2001

(65) Prior Publication Data

US 2002/0025256 A1 Feb. 28, 2002

Related U.S. Application Data

(63) Continuation of application No. 09/561,092, filed on Apr. 28, 2000, now Pat. No. 6,296,452.

(51) Int. Cl.$^7$ ................................................ F04B 19/24
(52) U.S. Cl. ..................................... 417/53; 417/413.2
(58) Field of Search ............................................ 417/53

(56) References Cited

U.S. PATENT DOCUMENTS

| 1,547,562 A | 7/1925 | Byrd |
| --- | --- | --- |
| 2,685,800 A | 8/1954 | Natelson |
| 2,737,812 A | 3/1956 | Haak |
| 3,622,279 A | 11/1971 | Moran |
| 3,716,338 A | 2/1973 | Moran |
| 3,972,683 A | 8/1976 | Lape |
| 4,525,728 A | 6/1985 | Koto |
| 4,526,046 A | 7/1985 | Oberli |
| 4,894,664 A | 1/1990 | Tsung Pan |
| 4,933,148 A | 6/1990 | Periman |
| 5,085,562 A | 2/1992 | van Lintel |
| 5,094,594 A | 3/1992 | Brennan |
| 5,101,673 A | 4/1992 | Uffenheimer et al. |
| 5,174,162 A | 12/1992 | Miyake et al. |
| 5,180,288 A | 1/1993 | Richteret et al. |
| 5,224,843 A | 7/1993 | van Lintel |
| 5,494,828 A | 2/1996 | Leopando |
| 5,550,059 A | 8/1996 | Boger et al. |
| 5,622,869 A | 4/1997 | Lewis et al. |
| 5,730,187 A | 3/1998 | Howitz et al. |
| 6,296,452 B1 * | 10/2001 | Caren ........................ 417/53 |

\* cited by examiner

Primary Examiner—Joseph Pelham
Assistant Examiner—L Fastovsky
(74) Attorney, Agent, or Firm—Gordon M. Stewart

(57) ABSTRACT

A microfluidic pumping apparatus and method using the apparatus. The apparatus may include a first pulse jet and working fluid in the pulse jet such that the first pulse jet, in response to activation by a set of electrical pulses, moves corresponding pulses of fluid from a first to an second side of the first pulse jet. A chamber with an opening is in pressure communication and with the first side of the first pulse jet such that activation of the first pulse jet causes a reduced pressure at the opening. The method comprising contacting the opening with a fluid and activating the first pulse jet so as to draw a sample fluid through the opening into the chamber. A second pulse jet, oppositely oriented from the first, may be provided to discharge loaded sample fluid.

8 Claims, 2 Drawing Sheets

MICROFLUIDIC PUMPING

This application is a continuation of Ser. No. 09/561,092 filed Apr. 28, 2000, now U.S. Pat. No. 6,296,452.

FIELD OF THE INVENTION

The present invention relates to methods and apparatus for pumping small volumes of fluid, particularly where small volumes of fluid are to be transferred from one container to the other.

BACKGROUND OF THE INVENTION

Automated liquid handling systems have become a standard part of many biological laboratories. In a typical configuration a robot or motion system is coupled with a syringe or peristaltic pump (such as the Biomek configuration by Beckman Coulter, Inc.). Such systems are fairly effective in transferring liquid samples in the 1 $\mu$l or larger range from one container to the other. However, they do not generally provide reliable transfer of sample volumes smaller than 1 $\mu$l.

Devices are known for through pumping of small fluid quantities. For example, U.S. Pat. Nos. 5,094,594, 5,730,187 and 6,033,628 disclose devices which can pump fluid volumes in the nanoliter or picoliter range. However, these devices are arranged so that the fluid sample is pumped through them. Such devices are not convenient for simply transferring fluid from one container to another where it is desired to aspirate and expel the fluid from the same opening in the manner of a pipette. This is so since with very small fluid samples some of the fluid will wet and remain in the pumping mechanism itself. The pumping mechanism then, becomes a source of sample cross-contamination unless cleaned.

It would be desirable then if a means could be provided which allowed for transfer of very small samples of relatively precisely controlled volume. It would further be desirable if such means allowed the surfaces contacted by the fluid to be separable and replaceable from the remainder of the device.

SUMMARY OF THE INVENTION

The present invention then, provides in one aspect a microfluidic pumping method. This method uses an apparatus with a pulse jet and a working fluid in the pulse jet. The pulse jet, in response to activation by a set of electrical pulses, moves corresponding pulses of fluid from a first to a second side of the pulse jet. A chamber with an opening, is in pressure communication with the first side of the pulse jet such that activation of the pulse jet causes a reduced pressure at the opening. The method includes contacting the opening (which in one particular aspect, may initially be open to ambient atmosphere but need not be in all aspects of the invention) with a sample fluid and activating the pulse jet so as to draw the sample fluid into the chamber (sometimes referenced as "loading" the sample). The chamber may or may not be partly empty of sample or any fluid before contacting the opening with the sample fluid. Optionally the opening and first side of the pulse jet may be in fluid isolation from one another, and the sample and working fluids may be maintained in isolation (that is, from one another), such as by an intervening gas (such as air) or liquid immiscible with the working and sample fluids, or by the sample and working fluids being different and immiscible with one another. Optionally, the method may include any suitable arrangement for discharging the loaded sample through the opening (for example, a second pulse jet as described further below). However, such arrangement need not allow for precise volume control of ejected sample since, with the sample and working fluids in isolation and when all the sample in the chamber is to be discharged, a precise volume was already determined by the pulse jet during sample loading into the chamber. Thus, the suitable arrangement mentioned could be a valve and pressure source for applying a pressure differential to the loaded sample.

Another aspect of the method uses an apparatus with a pulse jet head having first and second pulse jets and a working fluid in the head. The first pulse jet, in response to activation by a set of electrical pulses, moves corresponding pulses of fluid from a first side of the head to a second side. The second pulse jet, in response to activation by a set of electrical pulses, moves corresponding pulses of fluid from the second side of the head to the first side. A chamber with an opening is in pressure communication with the first side of the head, such that activation of the first pulse jet causes a reduced pressure at the opening and activation of the second pulse jet causes an increased pressure at the opening. In the aspect of the method, the opening is contacted with a sample fluid and the first pulse jet is activated so as to draw a sample fluid through the opening and into the chamber (that is, the sample is loaded). The second pulse jet may be activated so as to discharge loaded sample fluid through the opening.

Optionally, the opening may be a capillary opening, or the chamber may even comprise a capillary conduit which extends to the first pulse jet first side. Either configuration can assist in retaining sample fluid in the chamber prior to discharging it.

The present invention also provides a microfluidic pump of any of the configurations described above. The opening may be in pressure communication with the first side of the first pulse jet through, for example, a conduit shaped to maintain sample and working fluids in isolation. Such a configuration allows pressure communication but can maintain sample and working fluids in isolation from one another. Alternatively, a flexible diaphragm between the opening and the first side of the pulse jet head could be used for this purpose. Optionally, each pulse jet may have one or two check valves each on an inlet or outlet side of the pulse jet, to inhibit a backward flow through the pulse jets.

The various aspects of the present invention can provide any one or more of the following and/or other useful benefits. For example, very small volumes of samples can be transferred with relatively precisely control. It is not necessary that sample fluid contact internal pumping parts. The construction allows for surfaces contacted by the sample fluid to be separable and replaceable from the remainder of the device.

BRIEF DESCRIPTION OF THE DRAWINGS

Embodiments of the invention will now be described with reference to the drawings, in which.

DETAILED DESCRIPTION OF EMBODIMENTS OF THE INVENTION

Figure 2:
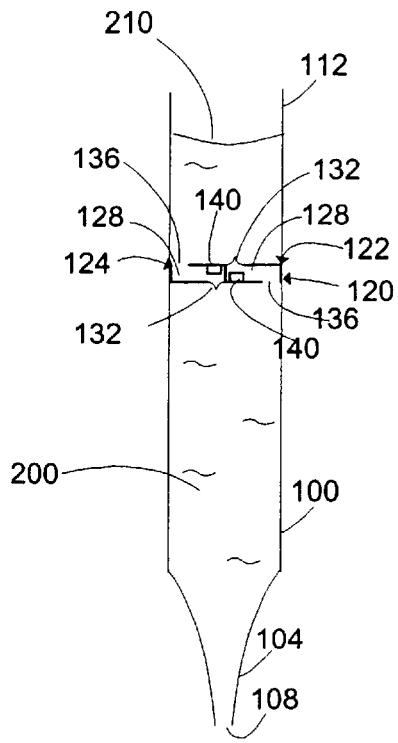
FIG. 2 is a cross-section through an alternate embodiment of a microfluidic pump of the present invention.

To facilitate understanding, identical reference numerals have been used, where practical, to designate like elements in the different FIGS.

In the present application, unless a contrary intention appears, the following terms refer to the indicated characteristics. Words such as "up" and "down" are used in a relative sense only, although they indicate a typical (but not essential) orientation during apparatus use. A "fluid" is used to reference a liquid. Reference to a singular item, includes the possibility that there are plural of the same items present. Potentials are relative. All patents and other cited references are incorporated into this application by reference.

Figure 1:
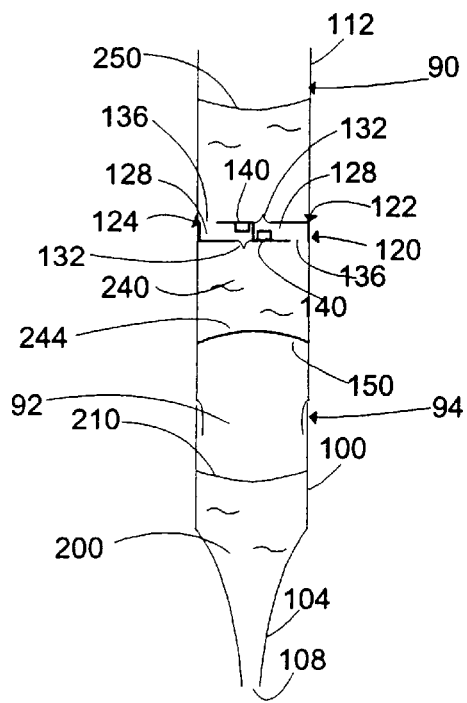
FIG. 1 is a cross-section through a microfluidic pump of the present invention, and illustrates its use.

Referring first to FIG. 1, the illustrated microfluidic pump has a tubular housing 90 of circular cross-section, defining a conduit which particularly includes a chamber 92 defined by lower end 100 of housing 90. Lower end 100 includes a tip 104 (which need not be tapered) with an opening in the form of orifice 108. Lower end 100 may be detachable from the remainder of housing 90 with an appropriate joint such as joint 94. A pulse jet head 120 is fitted within housing 90 at a position intermediate lower end 100 and an upper end 112 of housing 90. Pulse jet head 120 includes a first pulse jet 122 and second pulse jet 124. Each pulse jet 122, 124 has an inlet 136 and an outlet defined by a check valve 132, a pulse jet chamber 128, and a pulse element 140. Pulse jets 122, 124 may be of identical construction and such as found in a typical ink jet printer head, with pulse element 140 being a piezoelectric element or a resistor in a manner well known in the ink jet printing art. Each of the pulse jets 122, 124, in response to activation by a set of electrical pulses, will move corresponding pulses of a working fluid in chamber 128 from the inlet to the outlet. In particular, first pulse jet 122 moves working fluid from a first side (the lower side as viewed in FIG. 1) of head 120 to an second side (the upper side as view in FIG. 1), while second pulse jet 124 moves working fluid from the second side to the first side (that is, pulse jets 122, 124 move fluid in opposite directions). An optional flexible membrane 150 may extend across an inside of housing 90 at a position between chamber 92 and the first side of the pulse jet head 120. Note that since housing 90 is continuous, orifice 108 is in pressure communication with the first side of head 120. If membrane 150 is not present, orifice 108 will also be in fluid communication with the first side of head 120. When membrane 150 is not present though, housing 90 is preferably dimensioned to define therein a capillary conduit which extends between orifice 108 to the first side of the pulse jet. By "capillary" in this context, is referenced a sufficiently narrow dimensions such that a fluid (such as water or an aqueous solution) can be retained in place in housing 90 by surface tension.

As is well known in the ink jet print art, the amount of fluid that may be expelled by a pulse jet 122, 124 in a single activation event (that is, one pulse), can be controlled by changing one or more of a number of parameters, including the outlet diameter, the outlet length (thickness of the member in which the outlet opening is defined), the size of the chamber 128, and the size of the element 140, among other factors. The amount of fluid that is ejected through the outlet during a single activation event is generally in the range about 0.1 to 1000 picoliters ("pL"), usually about 0.5 to 500 pL and more usually about 1.0 to 250 pL. A typical velocity at which the fluid is expelled from the chamber is more than about 1 m/s, usually more than about 10 m/s, and may be as great as about 20 m/s or greater. However, the volumes and velocities will also depend to some extend on any external pressure at the inlet and outlet.

The operation of the microfluidic pump described in FIG. 1 will now be described. It will be assumed initially that membrane 150 is not present, and housing 90 defines a capillary conduit. First, a quantity of working fluid 240 is drawn in through orifice 108. This can be accomplished by touching tip 108 to a quantity of working fluid. Since housing 90 defines a capillary conduit, the working fluid will be drawn by surface tension up through orifice 108 and into chamber 92. The working fluid 240 is allowed to rise until it reaches head 120. A reduced pressure can be applied from an external pump (not shown) and/or pulse jets 122, 124 can be fired, as needed until the situation shown in FIG. 1 is obtained, wherein upper and lower surfaces 250, 240 of the working fluid are in the positions shown in FIG. 1. Capillary pressure assists in retaining working fluid 240 in the position shown in FIG. 1. Note that during such loading of the working fluid 240, air or another gas (such as nitrogen), or a liquid immiscible with working and sample fluids 240, 200, can be drawn up behind working fluid 240.

To load a sample fluid 200 into chamber 92, orifice 108 is placed in contact with the sample fluid and first pulse jet 120 repeatedly activated. Since orifice 108 is in pressure communication (and fluid communication) with the first side of pulse jet head 120, such activation causes a reduced pressure at the orifice 108 so as to draw sample fluid 200 through orifice 108 and into chamber 92. Following this, the pump of FIG. 1 can optionally be moved to another location for dispensing sample fluid 200. Note that sample fluid 200 and working fluid 240 are isolated from one another by intervening gas between upper surface 210 of loaded sample fluid 200 and lower surface 244 of working fluid 240. The fact that orifice 108 is also capillary sized (as is the chamber 92) assists in retaining loaded sample fluid 200 in chamber 92. To unload or discharge sample fluid 200, second pulse jet 124 is repeatedly activated. This will increase pressure on the first side of head 120 so as to discharge loaded sample fluid 200 through orifice 108.

At this point it should be understood that valves 132 should not only close to prevent backward flow through pulse jets 122, 124, but should also provide some resistance to permitting forward flow through them. If this were not so, when first pulse jet 122 had increased the height of surface 250 of working fluid 240, that fluid may tend to flow back downward through valve 132 of second pulse jet 124. Thus, the resistance of valves 132 to forward flow should be sufficient to prevent such flow during normal operation while still being capable of being opened upon activation of element 140. Particular valves which may be used are those such as disclosed in U.S. Pat. No. 5,085,562. Alternatively, valves 132 could be electrically controlled valves which are opened from a normally closed position, in synchronization with firing of a corresponding element 140. Various mechanical and electrically operated microvalves are described, for example in U.S. Pat. Nos. 5,094,594; 5,224,843; 6,033,628; and the references cited therein, all of which are incorporated herein by reference.

In an alternative arrangement housing 90 need not be dimensioned to provide a capillary conduit therein (although orifice 108 may still be a capillary sized orifice), in which case flexible membrane 150 may be present to retain the working fluid in position about head 120 while still allowing lower or higher pressure created on the first side of head 120 to be communicated to orifice 108 to load or discharge sample fluid, respectively. It will also be appreciated that it is not essential that orifice 108 be a capillary sized orifice.

Instead, a non-capillary sized orifice could be used in conjunction with an electrically operated valve system (similar to an electrically operated valve such as mentioned above) activated externally in synchronization with activation of pulse jets 122, 124 to allow loading or discharging, respectively, of sample fluid. Such a valve would retain loaded sample fluid 200 in chamber 92 prior to activating second pulse jet 124.

FIG. 2 illustrates essentially the same microfluidic pump as in FIG. 1. However, in FIG. 2 flexible membrane 150 is not present. Also, the microfluidic pump of FIG. 2 is illustrated in a somewhat different use than in FIG. 1. In particular, in the case of FIG. 2 the working fluid is the same as the sample fluid, and thus it is not required they be isolated from one another. Otherwise, the microfluidic pump of FIG. 2 may be of essentially the same construction as that of FIG. 1 (including variations already mentioned in connection with FIG. 1), and operated in a similar manner. This method is particularly useful where the microfluidic pump is being used to repeatedly transfer small volumes of the same sample fluid.

Figure 3:
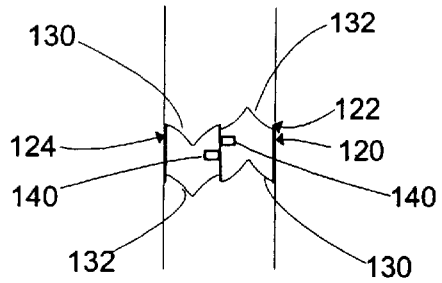
FIG. 3 illustrates an alternate pulse jet head valve configuration.

FIG. 3 illustrates an alternate valve mechanism which may be used with each pulse jet. In particular, if larger valves are desired then valves 132 may be made much larger as illustrated in FIG. 3. In such a case, since element 140 may be further away from a corresponding valve 132, a second check valve 130 may be provided on an inlet side of each pulse jet 122, 140 to permit forward flow of working fluid through the pulse jet. In this configuration, each pair of valves 130, 132 will inhibit backward flow through their corresponding pulse jet. Each valve 130 may be of any of the constructions of valve 132 as mentioned above.

Figure 4:
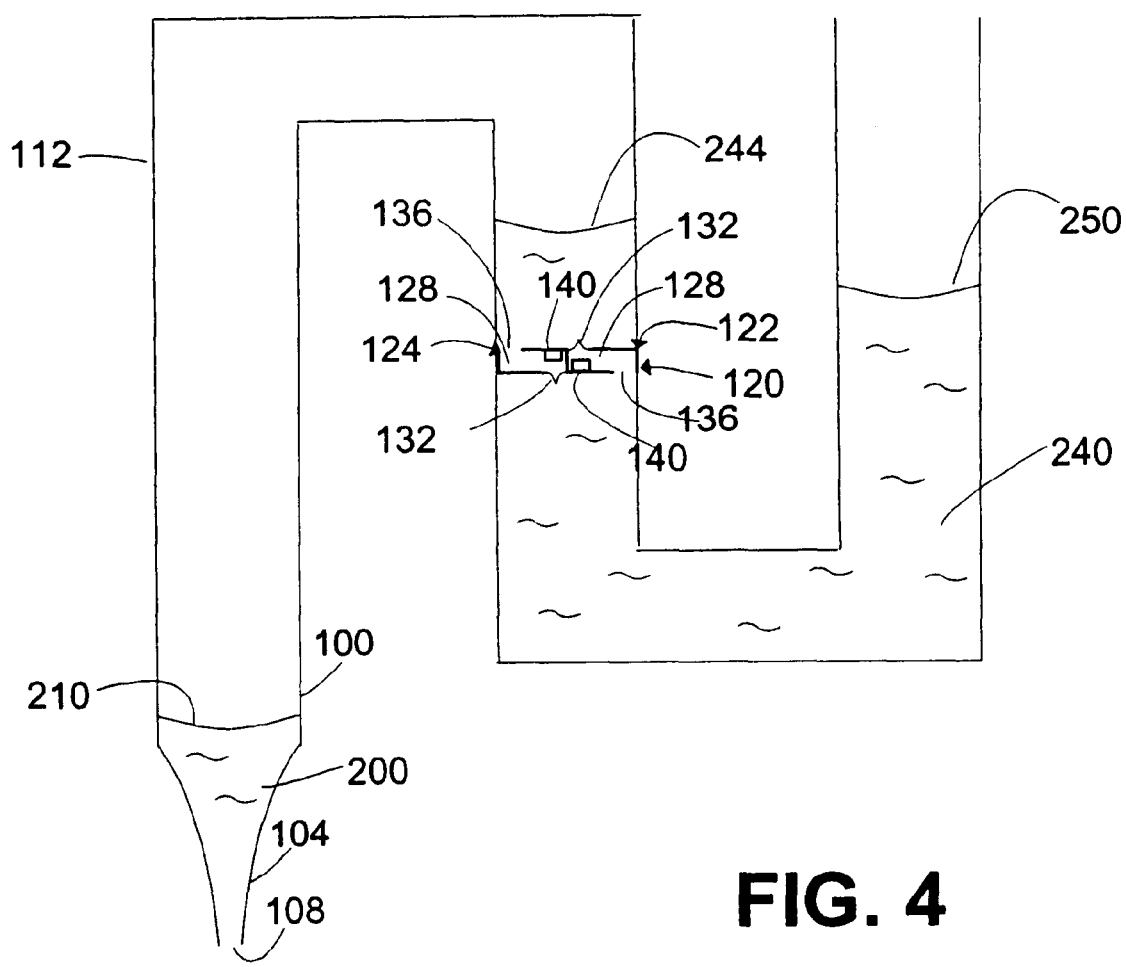
FIG. 4 is a cross-section through a further embodiment of a microfluidic pump of the present invention.

The embodiment of the microfluidic pump illustrated in FIG. 4 is similar in construction and use as that of FIG. 1 (and may include any of the variations mentioned in connection with FIG. 1). However, in FIG. 4 the passage defined by housing 90 is shaped to maintain working and sample fluids in isolation and to retain working fluid 240 about head 120. Thus, flexible membrane 150 need not be used and the passage defined by housing 90 need not be capillary (although orifice 108 may be capillary, or may not be when a valve is used as described above).

In a typical construction of a microfluidic pump as shown in the FIGS., the inside cross-sectional area within the conduit defined by housing 90 may be in the order of about 1 $\mu$m to 1 mm, usually about 5 $\mu$m to 100 $\mu$m, and more usually about 10 $\mu$m to 60 $\mu$m, with orifice 108 having the same or less cross-sectional areas. However, this will vary depending upon the sample fluid volume to be loaded and dispensed. Typical volumes of a sample fluid which may be loaded into chamber 92 may be between 0.1 pL to 100 $\mu$L, usually 1 pL to 250,000 pL, and more usually 10 pL to 25,000 pL (or even 100 pL to 2500 pL). The dimensions of the housing 90 and pumping capacity of head 120 can be adjusted according to the sample fluid volumes to be loaded and discharged, and according to the precision requirements in the loaded and discharged volumes. For larger volumes in particular, multiple first pulse jets 122 and multiple second pulse jets 124 can be present and used in synchronization to speed up the rate of sample fluid loading or discharging. It will be understood that a suitable processor (which includes a programmable processor, such as a digital processor) and power supply may be provided (not shown) to activate head 120 and optionally, any electrically controlled valves as discussed above in co-ordination with head 120. In a variation of the particular embodiments described above, only one pulse jet is provided for loading fluid. In this case though, some other suitable arrangement to discharge the loaded sample fluid through orifice 108. Such suitable arrangement could be a valve and pressure source communicating with chamber 92 for applying a pressure differential to the loaded sample.

With the microfluidic pumps described above, very precise control of the volume loaded or discharged, can be obtained. Additionally, in the case where the working fluid is maintained in isolation from the sample fluid, lower end 100 can be detached at joint 94 and replaced with a new lower end 100 when a different sample fluid is to be loaded, thereby preventing sample cross-contamination. The working components (particularly head 120) is not contacted by sample fluid in this configuration and hence need not be cleaned or replaced.

Various further modifications to the particular embodiments described above are, of course, possible. Accordingly, the present invention is not limited to the particular embodiments described in detail above.

What is claimed is:

1. A microfluidic pump comprising:

first and second pulse jets such that the first pulse jet, in response to activation by a set of electrical pulses, moves corresponding pulses of fluid from a first side to a second side, and the second pulse jet, in response to activation by a set of electrical pulses, moves corresponding pulses of fluid from the second side to the first side.

2. A microfluidic pump according to claim 1 additionally comprising first and second check valves communicating with respective pulse jets to inhibit a backward flow through the pulse jets.

3. A microfluidic pump according to claim 1 wherein a conduit communicates with the first side.

4. A microfluidic pump according to claim 1 wherein the conduit is a capillary conduit.

5. A microfluidic pumping method using a microfluidic pump according to claim 1, comprising:

(a) activating the first pulse jet so as to move fluid from the first side to the second side; and (b) activating the second pulse jet so as move fluid from the second side to the first side.

6. A microfluidic pumping method using a microfluidic pump according to claim 2, comprising:

(a) activating the first pulse jet so as to move fluid from the first side to the second side; and (b) activating the second pulse jet so as move fluid from the second side to the first side.

7. A microfluidic pumping method using a microfluidic pump according to claim 3, comprising:

(a) activating the first pulse jet so as to move fluid from the first side to the second side; and (b) activating the second pulse jet so as move fluid from the second side to the first side.

8. A microfluidic pumping method using a microfluidic pump according to claim 4, comprising:

(a) activating the first pulse jet so as to move fluid from the first side to the second side; and (b) activating the second pulse jet so as move fluid from the second side to the first side.

* * * * *